US012628750B2

(12) United States Patent　　　　(10) Patent No.: US 12,628,750 B2
Bullock et al.　　　　　　　　　　(45) Date of Patent:　May 19, 2026

(54) PLANT CELL CHROMOSOME DOUBLING BY APPLICATION OF ELECTROMAGNETIC FIELD

(71) Applicants: SYNGENTA CROP PROTECTION AG, Basel (CH); Purdue Research Foundation, West Lafayette, IN (US)

(72) Inventors: William Paul Bullock, Research Triangle Park, NC (US); Rachel L. Egger, Research Triangle Park, NC (US); Allen L. Garner, West Lafayette, IN (US); Aginiprakash Dhanabal, West Lafayette, IN (US)

(73) Assignees: PURDUE RESEARCH FOUNDATION, West Lafayette, IN (US); SYNGENTA CROP PROTECTION AG, Basel (CH)

( * ) Notice: Subject to any disclaimer, the term of this patent is extended or adjusted under 35 U.S.C. 154(b) by 22 days.

(21) Appl. No.: 18/037,710

(22) PCT Filed: Nov. 19, 2021

(86) PCT No.: PCT/US2021/060144
§ 371 (c)(1),
(2) Date: May 18, 2023

(87) PCT Pub. No.: WO2022/109303
PCT Pub. Date: May 27, 2022

(65) Prior Publication Data
US 2024/0023504 A1　　　Jan. 25, 2024

Related U.S. Application Data

(60) Provisional application No. 63/116,555, filed on Nov. 20, 2020.

(51) Int. Cl.
*A01H 1/08*　　　(2006.01)
*A01H 1/06*　　　(2006.01)
*A01H 6/46*　　　(2018.01)

(52) U.S. Cl.
CPC ................ *A01H 1/08* (2013.01); *A01H 1/09* (2021.01); *A01H 6/4684* (2018.05)

(58) Field of Classification Search
None
See application file for complete search history.

(56) References Cited

U.S. PATENT DOCUMENTS

| | | |
|---|---|---|
| 2003/0005479 A1 | 1/2003 | Kato |
| 2008/0216191 A1 | 9/2008 | Barton et al. |
| 2011/0137229 A1 | 6/2011 | Palti et al. |

FOREIGN PATENT DOCUMENTS

| | | |
|---|---|---|
| CA | 1341049 A | 7/2000 |
| JP | 11511974 A | 10/1999 |
| JP | 2007174946 A | 7/2007 |
| WO | 2013011507 A1 | 1/2013 |

OTHER PUBLICATIONS

Salma et al., Artificial polyploidy in medicinal plants: Advancement in the last two decades and impending prospects, 2017, Journal of Crop Science and Biotechnology, vol. 20, pp. 9-19 (Year: 2017).*
Tkalec et al., Effects of radiofrequency electromagnetic fields on seed germination and root meristematic cells of *Allium cepa* L., 2009, Mutation Research/Genetic Toxicology and Environmental Mutagenesis, vol. 672(2), pp. 76-81 (Year: 2009).*
WHO, 2016, Radiation: Electromagnetic fields, https://www.who.int/news-room/questions-and-answers/ item/radiation-electromagnetic fields#:~:text=Natural%20sources%20of%20electromagnetic%20fields, birds%20and%20fish%20for%20navigation (Year: 2016).*
Radic et al., Radio frequency electromagnetic field (900 MHz) induces oxidative damage to DNA and biomembrane in tobacco shoot cells (*Nicotiana tabacum*), 2007, IEEE/MTT-S International Microwave Symposium, Honolulu, HI, pp. 2213-2216 (Year: 2007).*
Zaidi et al., Effects of Electromagnetic Fields (Created by High Tension Lines) on Some Indigenous Plant Species—V. *Boraginaceae juss., Brassicaceae burnett* and *Caesalpiniaceae R*. Br., 2018, Pak. J. Bot., vol. 50(6), pp. 2237-2244 (Year: 2018).*
Akbal et al., Effects of Electromagnetic Waves Emitted by Mobile Phones on Germination, Root Growth, and Root Tip Cell Mitotic Division of Lens culinaris Medik, 2012, Pol. J. Environ. Stud., vol. 21(1), pp. 23-29 (Year: 2012).*
Tkalec et al., Influence of 400, 900, and 1900 MHz Electromagnetic Fields on Lemna minor Growth and Peroxidase Activity, 2005, Bioelectromagnetics, vol. 26, pp. 185-193 (Year: 2005).*
Vian et al., Plant responses to high-frequency electromagnetic fields, 2016, BioMed Research International, vol. 2016(1830262), pp. 1-13 (Year: 2016).*
Kumar et al., EMF radiations (1800 MHz)-inhibited early seedling growth of maize (*Zea mays*) involves alterations in starch and sucrose metabolism, 2016, Protoplasma, vol. 253, 1043-1049 (Year: 2016).*
Trifunovic, N., Earth's Arth's Magnetic Field is Factor that Frges Cell Divsion. Reducing Cell's Magnetic Characteristics Occurs Aging and Death, 2020, Journal of Cancer Research Reviews & Reports, vol. 2(1), pp. 1-7 (Year: 2020).*
Hush , et al., "Electrical and Mechanical Fields Orient Cortical Microtubules in Higher Plant Tissues", Cell Biology International Reports, vol. 15, No. 7, Jul. 1991, pp. 551-560.
PCT/US2021/060144 , "International Preliminary Report on Patentability", Jun. 1, 2023, 6 pages.
PCT/US2021/060144 , "International Search Report and Written Opinion", Feb. 18, 2022, 7 pages.

(Continued)

*Primary Examiner* — Bratislav Stankovic
*Assistant Examiner* — Christina L Meadows
(74) *Attorney, Agent, or Firm* — Kilpatrick Townsend & Stockton LLP

(57) ABSTRACT

Disclosed are methods for the doubling of a plant cell's chromosome by applying an electromagnetic field and methods for obtaining a doubled-haploid plant cell. In some embodiments, the plant cell is selected from the group comprising maize, rice, tomato, and tobacco. Also disclosed is an apparatus for applying an electromagnetic field to a plant cell.

22 Claims, 3 Drawing Sheets

(56)                References Cited

OTHER PUBLICATIONS

Chandel , et al., "Appraisal of Immediate and Late Effects of Mobile Phone Radiations At 2100 Mhz on Mitotic Activity and Dna Integrity in Root Meristems Of Allium Cepa", Protoplasma, vol. 256, No. 5, May 21, 2019, pp. 1399-1407.

EP21895693.6 , "Extended European Search Report", Sep. 11, 2024, 10 pages.

Kumar , et al., "Emf Radiations (1800 Mhz)-inhibited Early Seedling Growth Of Maize (*Zea Mays*) Involves Alterations in Starch and Sucrose Metabolism", Protoplasma, vol. 253, No. 4, Aug. 16, 2015, pp. 1043-1049.

Maqbool , et al., "Doubled Haploids in Maize: Development, Deployment, and Challenges", Crop Science, vol. 60, No. 6, Jul. 18, 2020, pp. 2815-2840.

Shabrangi , et al., "Effects of Extremely Low Frequency Electromagnetic Fields on Growth, Cytogenetic, Protein Content and Antioxidant System of *Zea Mays* L", African Journal of Biotechnology, vol. 10, No. 46, Aug. 22, 2011, pp. 9362-9369.

Vian , et al., "Plant Responses to High Frequency Electromagnetic Fields", Biomed Research International, vol. 2016, Jan. 1, 2016, 13 pages.

Berkelmann et al., "Tumour-treating fields (TTFields): Investigations on the Mechanism of Action by Electromagnetic Exposure of Cells in Telophase/Cytokinesis", Scientific Reports, vol. 9, No. 7362, May 14, 2019, pp. 1-11.

Uppalapati et al., ""Artificial Mitotic Spindle" Generated by Dielectrophoresis and Protein Micropatterning Supports. Bidirectional Transport Of Kinesin-Coated Beads", Integrative Biology (Camb), vol. 3, No. 1, Available online at: https://www.ncbi.nlm.nih.gov/pmc/articles/PMC3071969/>, Jan. 11, 2011, 15 pages.

* cited by examiner

PLANT CELL CHROMOSOME DOUBLING BY APPLICATION OF ELECTROMAGNETIC FIELD

CROSS-REFERENCES TO RELATED APPLICATIONS

This application is a 371 National Stage of PCT Application No. PCT/US2021/060144, filed Nov. 19, 2021, which claims the benefit of and priority to U.S. Provisional Application No. 63/116,555, filed on Nov. 20, 2020, the entire disclosure of each of which are herein incorporated by reference for all purposes.

FIELD

This disclosure relates to methods of making doubled-haploid plants and doubled-haploid seed in order to accelerate plant breeding, and apparatuses in support thereof.

BACKGROUND

Doubled haploid plants are widely used in modern plant breeding programs. Typically, this involves obtaining a haploid plant as the product of a cross between a normal plant and a haploid inducer plant, or by culturing haploid gametophytes into haploid sporophytes via microspore culture, anther culture, ovule culture, or ovary culture. Haploid plant sporophytes, absent some form of spontaneous chromosome doubling, are sterile if allowed to develop without further human intervention and contain only half the normal number of chromosomes for that plant species. See S. T. Chalyk, *Properties of maternal haploid maize plants and potential application to maize breeding*, EUPHYTICA 79:13-18 (1994), at 14, col. 2. For example, maize is considered a diploid organism comprising 20 chromosomes (i.e., two copies of each set of 10 distinct chromosomes). See, e.g., M. P. Maguire, *Chromosome behavior at premeiotic mitosis in maize*, J. HEREDITY 74:93-96 (1983), at Table 1. In comparison, a haploid maize plant contains only 10 chromosomes (i.e., one copy of each of the 10 chromosomes). To make a haploid plant fertile, the chromosome complement must be doubled, at least in the male and female reproductive lineages, if not the whole plant.

Interspecific hybridization is a widely used technique in modern and historic plant breeding programs. Typically, this involves crossing two plants together from different species or subspecies to produce a hybrid with two sets of different chromosomes. In plant breeding, such a cross is frequently used to introgress traits from a wild relative into a domesticated crop species, or to introgress traits from one domesticated species into another. Examples from plant breeding include wheat-by-rye interspecific hybrids and *Brassica rapa*-by-*oleracea* interspecific hybrids. Interspecific hybrids are often partially or completely sterile due to chromosome pairing and meiotic segregation issues. In order to convert interspecific hybrid plants from sterile to fertile, their chromosomes are doubled through mitotic inhibition, described below.

Doubling of a plant's chromosomes is typically accomplished using a liquid mitotic spindle poison(s)—toxic chemicals sometimes used in treating cancers in humans or which chemicals may be antimicrotubule herbicides. See Y. Wan, et al., *The use of antimicrotubule herbicides for the production of doubled haploid plants from anther-derived maize callus*, THEOR. APPL. GENET. 81 (2): 205-211 (1991). Alternatively, nitrous oxide gas may be used to achieve chromosome doubling. Anti-mitotic chemicals interfere with a cell's ability to assemble microtubules and form spindle fibers necessary for cell division during mitosis. In the case of cancer treatments, the toxins are used to interfere with mitosis for a period of time so as to cause cell death. See Z. Y. Lin, et al., *Anticancer effects of clinically acceptable colchicine concentrations on human gastric cancer cell lines*, J. MED. SCI. 32 (2): 68-73 (2016). The cells cannot divide; the cells die. With plants, these toxins will also cause cell death if the cells are exposed for too long (referred to as the "lethal period"). Notably, DNA replication (that is, the doubling of a cell's chromosomes in anticipation of cell division) can proceed normally if the toxin is applied for less than the lethal period. Thus, a careful balance has to be struck between applying the toxin for a period that is sufficiently long to maximize the doubling of a haploid plant cell's chromosomes while inhibiting mitosis, yet sufficiently short enough to minimize cell death. This may be derisively called the "soak and hope" method.

Whether and for how long a plant cell can sustain the toxin depends on the plant species, tissue specificity, developmental stage, as well as the toxin itself. Colchicine is the predominant chromosome doubling agent ("CDA") used for plants; however, other known spindle poisons include trifluralin, pronamide, etc. See, e.g., A. M. Castillo et al., *Chromosome Doubling in Monocots*, at 331-332, in ADVANCES IN HAPLOID PRODUCTION IN HIGHER PLANTS (A. Toureav et al. eds., 2009); and Table 1 of U.S. Pat. No. 8,859,846, incorporated herein by reference in its entirety. In maize and many other species, haploid, diploid and interspecific hybrid embryos and seedlings are capable of surviving chromosome doubling with colchicine, although the survival rate is significantly less than 100%, and the fertility tends to remain low, usually less than 50%. Said another way, the treatment is often not very effective.

There are several challenges involved in the "soak and hope" method of applying a toxic CDA to haploid plant tissue. First, the CDA must be allowed sufficient time to penetrate into the target and permit DNA replication while inhibiting mitosis. Then, the CDA has to be removed before causing cell death. A secondary challenge lies in safe handling and proper disposal of the CDA. Thus, there exists a need to more effectively—and less lethally—interfere with mitosis in a plant cell, while additionally creating a safer environment for personnel practicing the doubling methods.

BRIEF SUMMARY

This summary is a high-level overview of various aspects of the present disclosure and introduces some of the concepts that are described and illustrated in the present document and the accompanying figures. This summary is not intended to identify key or essential features of the claimed subject matter, nor is it intended to be used in isolation to determine the scope of the claimed subject matter. The subject matter should be understood by reference to appropriate portions of the entire specification, any or all figures and each claim. Some of the exemplary embodiments of the present disclosure are discussed below.

The present disclosure is based in part on the development by the inventors of a method of doubling a plant cell's chromosomes by applying an electromagnetic field ("EMF"). The inventors have recognized that the EMF, when tuned to an effective frequency, and applied at a sufficient intensity, and/or for a sufficient duration, can disrupt the formation of spindle fibers without triggering cell death. When the EMF is applied during mitosis, plant cells undergo DNA replication without successfully completing mitosis. In effect, haploid or interspecific plant cells exposed to the EMF will double their chromosomes in the absence of a liquid spindle poison, and without incurring any of the lethal side-effects of the poison.

In one aspect, provided herein are methods for chromosome doubling in plant cells, comprising applying an EMF to a plant cell and allowing the EMF to disrupt mitosis, wherein the plant cell replicates its chromosomes without undergoing cell division, thereby obtaining a plant cell having doubled chromosomes. In some embodiments, the EMF disrupts mitosis by disrupting spindle fiber formation. In some embodiments, the EMF is applied at an effective frequency and intensity for a sufficient duration of application to disrupt mitosis in the plant cell. In some embodiments, the effective frequency is at a range of 1 kHz to 300 GHz, inclusive. In some embodiments, the sufficient duration of application is selected from the group consisting of (i) at least a duration equivalent to the prophase of mitosis for the plant cell; (ii) a duration equivalent to the entire mitosis cycle for the plant cell; and (iii) about 5 hours. In some embodiments, the duration equivalent to the prophase of mitosis is approximately 25 minutes for a maize cell.

In some embodiments of the methods provided herein, the applied EMF has a waveform, and parameters of the applied EMF include one or more of frequency, periodicity, and amplitude of the waveform.

In some embodiments of the methods provided herein, the plant cell is a monocot or a dicot. In some embodiments, the monocot is selected from the group consisting of maize, wheat, rice, sorghum, and barley. In some embodiments, the dicot is selected from the group consisting of soybean, sunflower, tomato, tobacco, cucurbits, brassicas, lettuce, *petunia*, rose, calliope, and onion. In some embodiments, the plant cell is a haploid plant cell. In some embodiments, the plant cell is a meristematic cell. In some embodiments, the plant cell is a gamete cell. In some embodiments, the plant cell is comprised within a tissue sample. In some embodiments, the tissue sample is a plant embryo. In some embodiments, the tissue sample is selected from the group consisting of a flower, an ear, a tassel, a seed pod, a seed, an embryo, and a portion of any of the preceding provided the tissue sample comprises viable cells.

Also provided herein are chromosome doubled plant cells produced by the methods herein. In some embodiments, the chromosome doubled plant cell is comprised within a plant embryo. Also provided herein are plants grown from the chromosome doubled plant cells and progeny therefrom.

Also included within the scope of this disclosure are apparatuses for applying an EMF to a plant cell for the purpose of doubling the chromosomes in the plant cell, whether the plant cell is comprised within an embryo, a microspore, callus tissue, a plant cell suspension, a whole plant (whether seedling or mature), male or female reproductive tissues of a whole plant, or any tissue comprising cells of the shoot apical meristem ("SAM"). In some embodiments, the apparatuses comprise a cavity for receiving a sample containing a plant cell, a circuit for generating and amplifying an EMF from power received from a power source, a receptacle for holding the plant cell in place in the cavity, and a pair of electrodes. In some embodiments, the apparatuses further comprise an oscilloscope for measuring the EMF applied to the plant cell and displaying an indication representative of the measured EMF.

In some embodiments of the apparatuses provided herein, the receptacle comprises the pair of electrodes. In some embodiments, the receptacle comprises a first pair of opposing electrodes arranged parallel to each other, wherein a separation between the pair of opposing electrodes defines the cavity for holding the plant cell. In some embodiments, the receptacle comprises insulated electrodes. In some embodiments, the receptacle comprises non-insulated electrodes. In some embodiments, the receptacle is a Petri dish comprising a cavity and optionally a medium. In some embodiments, the medium is a liquid medium, a solid medium, or a gaseous medium (e.g., air). In some embodiments, the Petri dish comprises the pair of electrodes. In some embodiments, the Petri dish comprises two electrode plates oriented in parallel and on opposite sides of the cavity such that the electrodes contact the medium. In some embodiments, the Petri dish comprises two electrode plates oriented in parallel and on opposite sides of the cavity such that one electrode contacts the medium and one electrode is configured to be separated from the medium by plastic or air. In some embodiments, the Petri dish comprises two electrode plates oriented in parallel and on opposite sides of the cavity such that the electrodes are configured to be separated from the medium by plastic or air. In some embodiments, the Petri dish includes an array of needle electrodes configured to be positioned around the sample to achieve a uniform electric field. In some embodiments, the Petri dish comprises a cover and wherein the needle electrodes penetrate the cover.

In some embodiments of the apparatuses provided herein, the receptacle is a cuvette comprising a cavity and optionally a medium. In some embodiments, the cuvette comprises the pair of electrodes. In some embodiments, the cuvette comprises two electrode plates oriented in parallel and on opposite sides of the cavity and configured so as to contact the medium. In some embodiments, the cuvette is an electroporation cuvette.

In some embodiments of the apparatuses provided herein, the pair of electrodes are a first pair of opposing electrodes and the apparatuses further comprise a second pair of opposing electrodes perpendicularly oriented with respect to the first pair of opposing electrodes. In some embodiments, the apparatuses further comprise a third pair of opposing electrodes perpendicularly oriented with respect to each of the first pair of electrodes and the second pair of electrodes.

In another aspect, provided herein are methods for producing a doubled-haploid plant cell comprising obtaining a haploid plant cell, subjecting the haploid plant cell to an EMF, and allowing the EMF to disrupt mitosis, whereby the haploid plant cell replicates its chromosomes yet fails to undergo cell division, thereby obtaining a doubled-haploid plant cell. In some embodiments, the EMF is an AC field with an applied electric field from 0.5 to 100 V/cm with frequency from 1 kHz to 300 GHz. In some embodiments, the EMF is an electric pulse with duration from 10 ns to 1 ms, applied electric field from 1 V/cm to 300 kV/cm, rise- and fall-times from 0.5 ns to 5000 ns, and repetition rate from 0.1 Hz to 100 Hz.

Also provided are doubled-haploid plant cells produced by the methods herein. In some embodiments, the plant cell is comprised within a plant embryo. In some embodiments, the plant embryo is a maize embryo. In some embodiments, the plant cell is comprised within a maize microsopore. Also provided herein are doubled-haploid plants grown from the doubled-haploid plant cells and progeny therefrom.

BRIEF DESCRIPTION OF THE DRAWINGS

The present disclosure includes the following figures. The figures are intended to illustrate certain embodiments and/or features of the methods and apparatuses, and to supplement any description(s) of the methods and apparatuses. The figures do not limit the scope of the methods and apparatuses, unless the written description expressly indicates that such is the case.

DETAILED DESCRIPTION

I. Terminology

Figure 1:
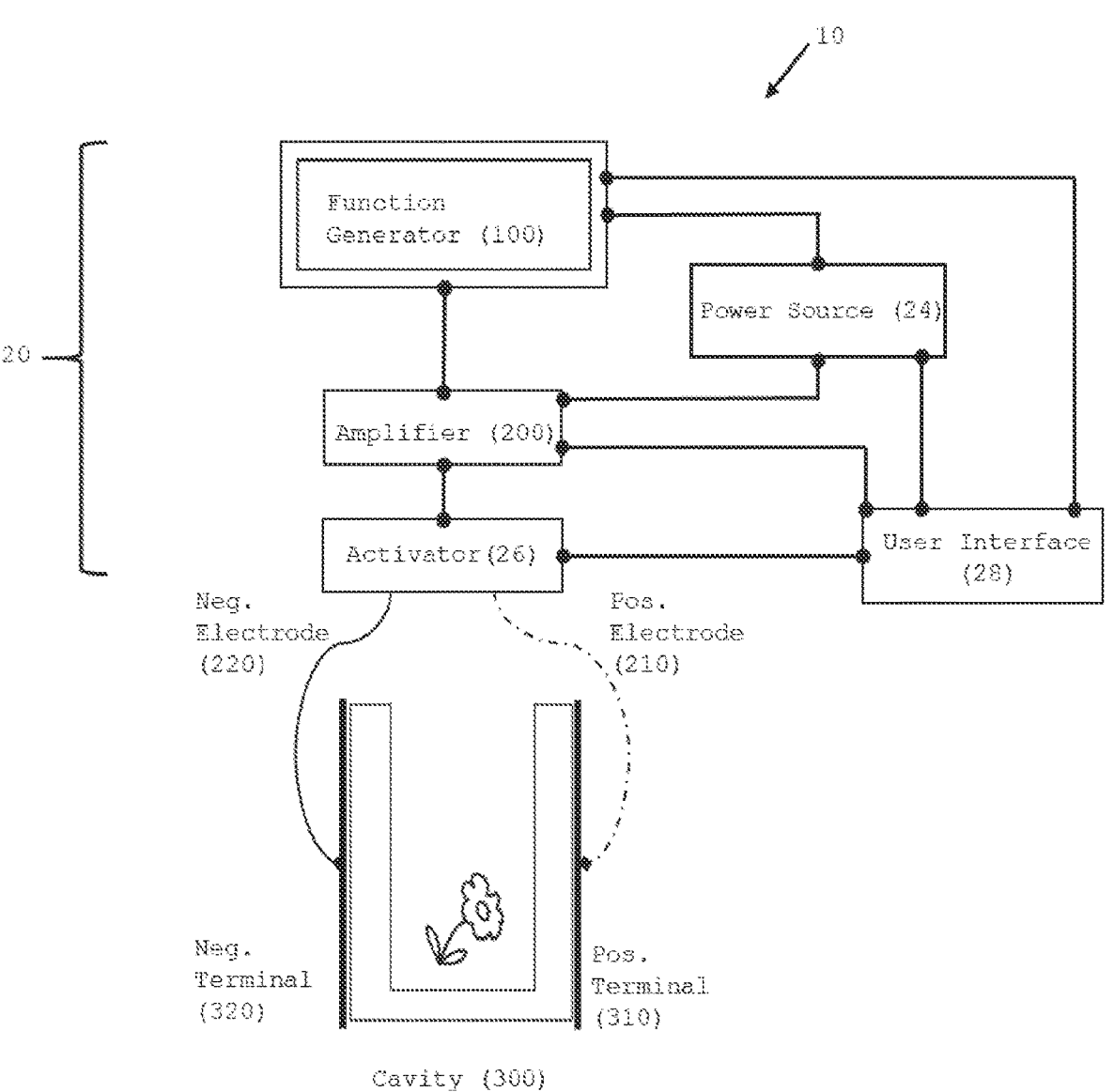
FIG. 1 shows an example embodiment of an apparatus for generating and applying an electromagnetic field (EMF) to a plant (or plant part).

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject.

As used in herein, the singular forms "a", "an" and "the" include plural referents unless the content clearly dictates otherwise. Thus, for example, reference to "an antibody" optionally includes a combination of two or more such molecules, and the like.

The term "about" as used herein refers to the usual error range for the respective value readily known to the skilled person in this technical field, for example ±20%, ±10%, or ±5%, are within the intended meaning of the recited value.

As used herein, the term "comprising" or "comprise" is open-ended.

The term "plurality" refers to more than one entity. Thus, a "plurality of individuals" refers to at least two individuals. A plurality may be 2, 3, 4, 5, 6, 7, 8, 9, 10, or more individuals within a larger population. Additionally, a plurality may be represented by 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, or 99% of the population.

A "plant" is any plant at any stage of development (e.g., a seed plant).

A "plant cell" is a structural and physiological unit of a plant, comprising a protoplast and a cell wall. The plant cell may be in form of an isolated single cell or a cultured cell, or as a part of higher organized unit such as, for example, plant tissue or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

The terms "tissue" or "sample" are used herein to mean any plant or plant part, including, but not limited to, anthers, microspores, embryos, liquid or solid plant tissue culture, plant callus, embryos, embryo-like structures, plantlets, seedlings, and young or mature plants, including plants growing in fields.

The term "progeny" refers to any plant resulting from a vegetative or sexual reproduction from one or more parent plants or descendants thereof. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

A plant referred to herein as "haploid" has a reduced number of chromosomes (n) in the haploid plant, and its chromosome set is equal to that of the gamete. In a haploid organism, only half of the normal number of chromosomes are present. Thus haploids of diploid (2n) organisms (e.g., maize) exhibit monoploidy (1n); haploids of tetraploid (4n) organisms (e.g., ryegrasses) exhibit diploidy (2n); haploids of hexaploid (6n) organisms (e.g., wheat) exhibit triploidy (3n); etc. As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric in vegetative tissues.

The term "cavity" as used herein refers to any object containing a space capable of holding, retaining, etc., a plant cell, plant tissue, plant embryo, plant meristem, or plant part. In some embodiments, the cavity may be made of metal, glass, plastic, or a combination thereof. The cavity may be a cuvette. The cavity may incorporate electrodes into the body of the object, or the cavity may be positioned near electrodes.

The term "chromosome doubling agent" ("CDA") refers to any toxin or chemical, such as colchicine, which is used to interfere with spindle fiber formation.

The terms "electromagnetic field," "EM field," and "EMF" are used interchangeably throughout. An EMF is a field containing both electric and magnetic components that results from the motion of an electric charge and contains a definite amount of electromagnetic energy. One may produce an EMF by transmitting alternating current along a wire/electrode/antenna as described in this disclosure. Another way of producing an EMF is by moving electrically charged objects. See generally RICHARD P. FEYNMAN ET AL., THE FEYNMAN LECTURES ON PHYSICS VOL. II, ISBN 978-0-201-02115-8 (Addison W. Longman, ed., 1970).

As used herein, "EMF application" to a sample includes the application of an electromagnetic field to a sample, optionally provided in a container, where the electromagnetic field is generated by an alternating current (AC) that is generally sinusoidal with respect to time (although it may have other temporal behavior). The electromagnetic field is defined by its magnitude (or peak electric field) and frequency (or period of the sinusoidal field). Additionally, "EMF application" means to expose a sample to EMF conditions.

The term "DNA replication" means the replication of a cell's entire genome, i.e., each of its chromosomes in anticipation of mitosis-regardless of whether mitosis is successfully completed or interrupted by some means.

The term "synchronize" as used herein refers to a state where a population of cells have been treated to ensure that a reasonable plurality of cells in the population (which may be as low as 1% but is preferably 30% or higher and optimally is above 80%) are at or near the same stage of cell division. Thus, when cells are synchronized, they are undergoing DNA replication at or near the same time and they are going through mitosis at or near the same time. In contrast, a population of cells that has not been synchronized comprises cells at various stages from interphase to cell division, including DNA replication and mitosis, regardless of the point in time.

"Wide cross," "wide hybridization," "interspecific crossing," "interspecific hybridization" and the like all refer to the forced breeding between unrelated or distantly-related species or varieties which are not—but for human intervention-capable of producing fertile or viable offspring. Wide crossing procedures usually rely on embryo rescue and may also involve chromosome doubling procedures. By way of example and not limitation, pollinating a maize flower with wheat pollen is a wide cross, and results in a haploid maize progeny.

II. Introduction

In anticipation of mitosis, a mother cell will undergo DNA replication and thus copy its genome so that each daughter cell, post cytokinesis of the mother cell, will comprise a complete copy of the mother cell genome. As a non-limiting example, a diploid maize cell normally comprises 20 chromosomes. After DNA replication, a mother maize cell will comprise 40 chromosomes. During mitosis, these chromosomes will be separated into two groups of 20 chromosomes, which will then form the genome for each daughter maize cell. As a non-limiting example, a haploid maize cell comprises 10 chromosomes. After DNA replication within said cell, the chromosomes have doubled to 20. By interrupting mitosis of the haploid cell at this stage and preventing cell division, the haploid maize cell becomes a doubled-haploid maize cell comprising the normal number of chromosomes: 20. As elaborated herein, the inventors have recognized that application of EMF to a plant cell can be advantageously used to interrupt mitosis and induce chromosome doubling. By adjusting the EMF applied to a plant sample (including a whole plant, a plant part, a plant cell, or plant tissue culture), such as by optimizing EMF amplitude, frequency, power setting, and waveform parameters, chromosome doubling can be achieved without affecting the viability of the plant sample. Without wishing to be bound by theory, it may be sufficient to interrupt mitosis during only the prophase sub-period of mitosis, in which spindle fibers are formed. However, current observations indicate that interrupting mitosis for all sub-periods of mitosis achieves the object of the method without the need for spindle fiber poisons.

III. Methods for Chromosome Doubling

In one aspect, provided herein are methods for inducing chromosome doubling in plant cells. In some embodiments, the methods comprise applying an electromagnetic field (EMF) to a plant cell and allowing the EMF to disrupt mitosis, as discussed above. In some embodiments, the EMF disrupts mitosis by disrupting spindle fiber formation. In some embodiments, the plant cell replicates its chromosomes (e.g., prior to EMF application, concurrently with EMF application, or after EMF application) without undergoing cell division, thereby obtaining a plant cell having double chromosomes.

Also provided herein are methods for producing a doubled-haploid plant cell, comprising obtaining a haploid plant cell, subjecting the haploid plant cell to an EMF, and allowing the EMF to disrupt mitosis. In some embodiments, the haploid plant cell replicates its chromosomes yet fails to undergo cell division, thereby obtaining a doubled-haploid plant cell.

In some embodiments, EMF application is optimized for a particular usage or for a particular outcome. For example, parameters of the applied EMF may be selected based on plant species and/or tissue type. In some embodiments, the applied EMF has a waveform. In some embodiments, parameters of the applied EMF (e.g., those selected based on plant species and/or tissue type) include one or more of frequency, periodicity, and amplitude of the EMF waveform. In some embodiments, parameters of the applied EMF may be selected based on type of medium, i.e., liquid media, solid media, or gaseous media (e.g., air), in which the plant tissue resides.

In some embodiments, the EMF is applied to a plant cell at an effective frequency and intensity for a sufficient duration of application to disrupt mitosis in the plant cell. In some embodiments, the frequency of the applied EMF is between 1 kHz and 300 GHz, or between 10 kHz and 1 GHz, or between 100 kHz and 500 kHz. In some embodiments, the intensity of EMF application is between 0.5 V/cm and 100 V/cm, or between 1.0 V/cm and 50 V/cm, or between 2.5 V/cm and 25 V/cm. In some embodiments, the EMF is an AC field with an applied electric field from 0.5 to 100 V/cm with frequency from 1 kHz to 300 GHz. In some embodiments, the EMF is an electric pulse with duration from 10 ns to 1 ms, applied electric field from 1 V/cm to 300 kV/cm, rise- and fall-times from 0.5 ns to 5000 ns, and repetition rate from 0.1 Hz to 100 Hz.

In some embodiments, the duration of application of the EMF is a time period that is sufficient to prevent mitosis in a sufficient number of cells in the embryo. In some embodiments, the duration allows for DNA replication without cell division, thereby causing chromosome doubling. The sufficient duration of EMF application may be at least 24 hours, or at least 12 hours, or at least 8, or at least 6 hours, or at least 4 hours, or at least 2 hours, or at least 1 hour, or at least 30 minutes. In some embodiments, the sufficient duration is about 15 minutes, about 30 minutes, about 45 minutes, about 1 hour, about 1.5 hours, about 2 hours, about 2.5 hours, about 3 hours, about 4 hours, about 5 hours, about 6 hours, about 7 hours, about 8 hours, about 9 hours, about 10 hours, about 12 hours, about 14 hours, about 16 hours, about 20 hours, about 24 hours, or more than 24 hours. In some embodiments, the sufficient duration of application is selected from the group consisting of (i) at least a duration equivalent to the prophase of mitosis for the plant cell (e.g., as known by one of skill in the art or as determined by experimentation); (ii) a duration equivalent to the entire mitosis cycle for the plant cell (e.g., as known by one of skill in the art or as determined by experimentation); and (iii) about 5 hours. In some embodiments (e.g., for a maize cell), the duration equivalent to the prophase of mitosis for the plant cell is approximately 25 minutes.

The methods of the present disclosure may be applied to a plant cell from any plant of interest. In some embodiments, the plant cell is a monocot or a dicot. In some embodiments, the monocot is selected from the group consisting of maize, wheat, rice, sorghum, and barley. In some embodiments, the dicot is selected from the group consisting of soybean, sunflower, tomato, tobacco, cucurbits, brassicas, lettuce, petunia, rose, calliope, and onion. In some embodiments, the plant cell is a haploid cell. In some embodiments, the plant cell is a meristematic cell. In some embodiments, the plant cell is a gamete cell. In some embodiments, the plant cell is comprised within a tissue sample. In some embodiments, the tissue sample is selected from the group consisting of a flower, an ear, a tassel, a seed pod, a seed, an embryo, and a portion of any of the preceding, provided the tissue sample comprises viable cells. In some embodiments, the tissue sample is a plant embryo.

Also provided herein are chromosome doubled plant cells and doubled-haploid plant cells produced by any of the methods described above. In some embodiments, the chromosome doubled plant cell or doubled-haploid plant cell is comprised within a plant embryo. In some embodiments, the plant embryo is a maize embryo. In some embodiments, the chromosome doubled plant cell or doubled-haploid plant cell is comprised within a maize microspore. Also provided are plants grown from the chromosome doubled plant cells, doubled-haploid plants grown from the doubled-haploid plant cells, and progeny of said plants.

IV. Apparatus for EMF Application

Figure 2:
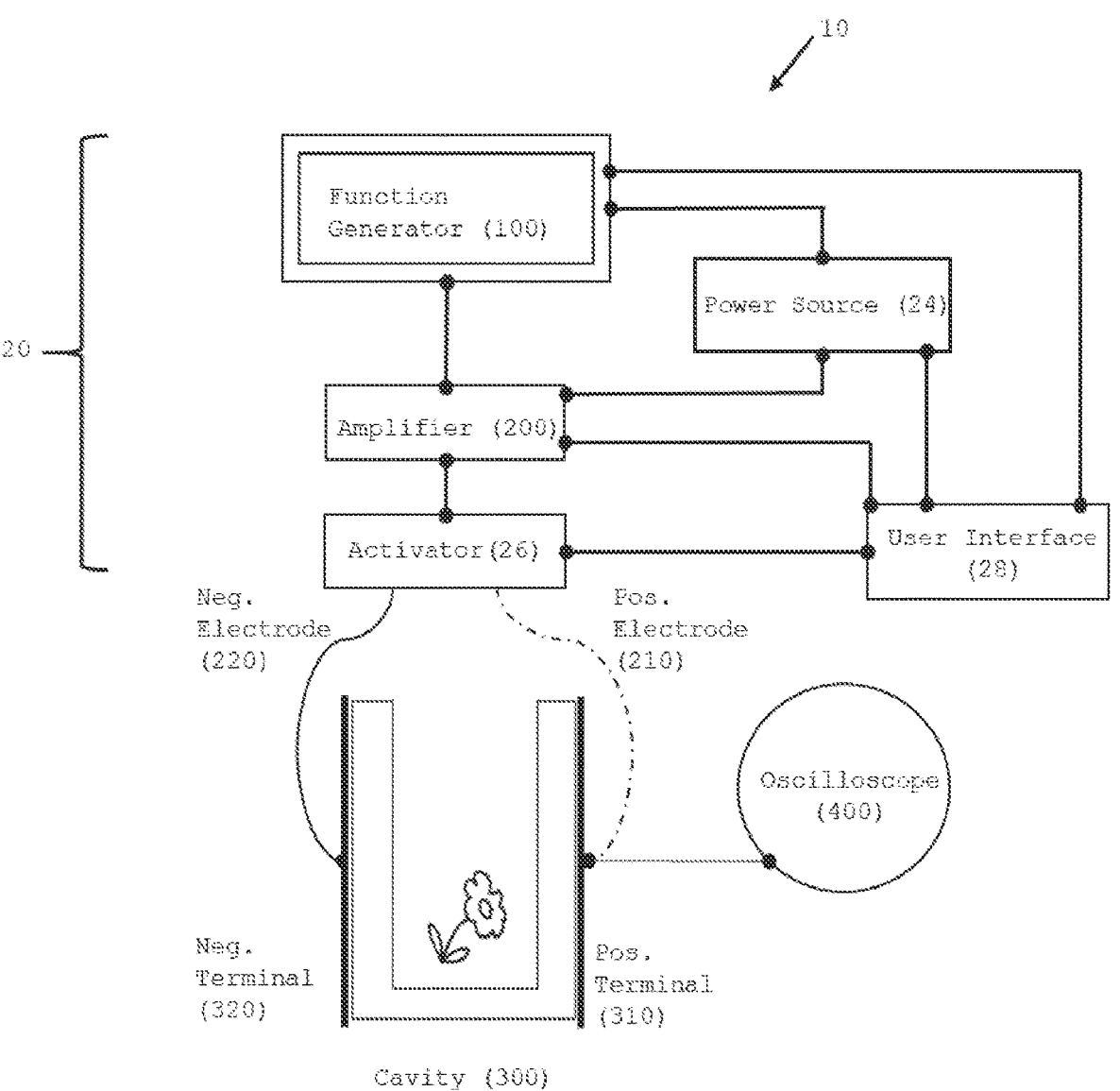
FIG. 2 shows another example embodiment of the apparatus embodiment of FIG. 1 comprising an oscilloscope.

FIGS. 1-2 show example embodiments of an apparatus that may be used for application of an electromagnetic field to a plant sample. Application of an electromagnetic field at an optimized field strength and frequency, and further optimized for duration of application, may result in chromosome doubling of a plant cell without degrading the viability of the cell. Particular methods are described with reference to the listed examples.

FIG. 1 shows an example embodiment of EMF apparatus (10) having a cavity 300 for receiving a plant sample (such as a whole plant or plant part or plant cell) and an electromagnetic circuit (20) configured to emit an electromagnetic field ("EMF") upon activation. The apparatus is configured to emit the field over an entire surface of the plant sample received in the cavity such that the radiated electromagnetic field impinges upon all the plant cells. In some implementations the apparatus is disposable and/or portable. A power source 24 supplies electricity to the apparatus.

The electromagnetic circuit 20 includes a Function Generator (100) operably linked to an Amplifier (200). The Function Generator ("FG") (100) comprises a field generator circuit printed on a circuit board. The Amplifier 200 includes an amplifier circuit printed on the same or a different circuit board. The FG 100 draws power from the power source 24 and generates the energy required for producing the EMF. Based on input from an apparatus user (such as a selected power setting), the FG is configured to produce a voltage at a selected combination of frequency and amplitude. As such, the FG may be capable of providing any pattern of voltages having any of a plurality of combinations of frequency and amplitude. As non-limiting examples, the FG may be capable of generating sine, square, saw-tooth or triangular waveforms. While the FG circuit is configured to create the various voltage waveforms, the amplifier is configured to amplify an input signal received from the FG. In some embodiments, the electrical circuits of the FG and the amplifier are printed on the same circuit board and housed in an electric housing that is separate from the remaining components of the EMF apparatus 10. In another example, the FG and amplifier circuits are printed on a control circuit chip to miniaturize the electrical components and improve portability of the apparatus. In some embodiments, based on the power requirement, amplification may not be required and the power output from the field generator is directly applied without amplification through the amplifier circuit.

An activator 26 can be used to initiate radiation of the electromagnetic field from the apparatus. The activator may include a switch that is a single-use or multiple use type and may be momentary or alternate-action. Actuation of the activator may be accomplished in various ways including manually by a user, by use of pressure, light or electronic signal either remotely or proximately. The activator 26 may be provided as part of a user interface 28 via which a user operates the device to generate and apply the EMF. Still other switches and buttons may be provided on the user interface. For example, the user interface may have a display via which a user may insert a desired parameter of the field to be applied, such as a frequency setting, a duration of field application setting, power setting, etc. Based on the user input received via the user interface 28, one or more settings of the power source, FG and/or amplifier may be adjusted to provide the EMF.

In some embodiments, the EMF apparatus includes a controller, such as a microcontroller or other computer processor that is operably coupled to the user interface and the FG circuit. The controller may include computer-readable instructions that can be executed to receive user input via the user interface and adjust parameters of the FG and/or amplifier circuits based on the received user input.

EMF apparatus 10 further comprises a pair of electrodes, specifically a Positive Electrode (210) and a Negative Electrode (220), that are operatively coupled to an output of the Amplifier 200 and FG 100. In other words, power from the FG 100 is amplified by the Amplifier 200 before being supplied to the electrodes 210-220. In embodiments where amplification is not required, power from the FG 100 can be directly supplied to the electrodes 210-220 while bypassing the amplifier 200. Power supplied from the power source 24 provides a first electrical signal to the positive electrode and a second electrical signal to the negative electrode, wherein the first and second electrical signals combine to produce the desired EMF of the selected frequency in a space between the electrodes. In one embodiment, the electrodes may be configured as wire electrodes. In another example embodiment, the pair of electrodes may be configured as rigid surfaces that define a structure of the apparatus, such as parallel metal plates having a central wire running through the plate. Further, a portion of the plates may be insulated. In another example, the electrodes may be configured as insulated stick electrodes having an elongated, rigid structure, a center wire of alloy steel, and an outer insulated coating.

The electrodes may be electrically coupled to a positive and negative terminal of the apparatus. Specifically, the Positive electrode 210 is coupled to the positive terminal 310 and the negative electrode 220 is coupled to the negative terminal 320. The positive and negative terminals may have a rigid surface. In one example, the positive and negative terminals may be configured as parallel metal plates wherein the space between the plates defines the cavity 300. When power is supplied from the power source 24 to the electrodes, the desired EMF of the selected frequency is created in the cavity 300 between the electrodes 310, 320. The cavity is where a plant sample (solid or liquid) is received and where the EMF is applied on the plant sample. In one example, where the plant sample includes liquid plant tissue culture medium, at least one of the terminals may be configured to make contact with the medium (e.g., at least one of the electrode plates of the cuvette may be positioned to make contact with the medium placed inside the cuvette).

A spacing of the rigid surface of the positive and negative terminals may be configured so that the cavity has a defined shape, size, or volume. In one example, the terminals are positioned and sized to accommodate a standard sized cuvette (e.g., an electroporation cuvette) in the cavity. In such an example, the terminals may include the electrode plates of the electroporation cuvette. In other examples, the terminals include electrodes incorporated within a petri dish such that the EMF can be applied within a cavity defined by the Petri dish. For example, the terminals may include an electrode array (e.g., needle electrode array) coupled to the Petri dish. In such an embodiment, an upper plate of the Petri dish may include perforations for receiving the needle electrode array there-though. The positioning of the array of needle electrodes through the perforations, and around the sample in the Petri dish allows for the application of a substantially uniform electric field through the sample in the Petri dish. In still other embodiments, the terminals are positioned to accommodate a beaker, flask, or other container in the cavity.

In embodiments wherein the cavity is sized to accommodate a Petri dish, and the terminals are configured as two electrode plates, the electrode plates may be oriented in parallel and on opposite sides of the cavity such that one of the electrodes contacts the medium while the other electrode is separated from the medium by plastic or air. In another example, the Petri dish comprises the two electrode plates oriented in parallel and on opposite sides of the cavity such that neither electrode contacts the medium and both electrodes are separated from the medium by plastic or air.

In a further embodiment, the apparatus may have a receptacle made of an insulated substrate or having an insulated coating. The receptacle may be configured to accommodate, therein, the cuvette or Petri dish in which the plant sample is held and on which the EMF is applied. Opposing sides of the receptacle may be coupled to the electrodes or terminals of the apparatus. For example, the opposing sides of the receptacle surface may have the positive and negative electrodes embedded therein. For example, the stick electrodes may have an exposed shaft at one end. The exposed shaft of the positive electrode may be embedded in one surface of the container, thereby defining the positive terminal of the container, and the exposed shaft of the negative electrode may be embedded in an opposing surface of the container, thereby defining the negative terminal of the container. Alternatively, non-insulated electrodes may be embedded inside the opposing container surfaces. In such an apparatus, the Positive Electrode (210) connects to the Positive Terminal (310) of the container and the Negative Electrode (220) connects to the Negative Terminal (320). A plant cell, plant tissue, plant embryo, or plant resides in the Cavity (300). Based on the desired implementation, the receptacle may be shaped and sized to accommodate a container in which the plant sample is placed. As non-limiting examples, the receptacle may be shaped and sized to accommodate a cuvette, a Petri dish, a beaker, a flask, etc. When accommodated in the receptacle, the container holding the plant sample is held in a snug fit in the cavity, and EMF is applied on the sample via the electrodes embedded in the receptacle surface.

In some embodiments, an indicator can be provided that is configured to exhibit indicia that the EMF apparatus is active and that an EMF is being applied in the cavity. The indicator, when included, may include one or more of a visual indicator such as a light emitting diode (LED), lamp or electro-luminescent display; an auditory indicator such as noise generator; or a tactile indicator such as a vibrator. In various implementations, the indicator may be steady, intermittent or pulsed.

In one example embodiment, the indicator may be coupled to an electromagnetic field detector in the control circuit chip and indicate the presence or absence of EMF generation from the device. Further, the indicator may enable measurement of the applied EMF. FIG. 2 shows an alternate embodiment of the apparatus of FIG. 1 including an Oscilloscope (400) operably linked to the Cavity (300) to observe and measure the EMF present in the Cavity (300). This enables a user to measure the EMF to which the plant cell, plant tissue, plant embryo, or plant is subjected.

In some embodiments, the apparatus is portable enabling the EMF to be applied to a plant in a field. For example, the electrodes and terminals may be positioned such that a field plant, or a part of a field plant, can be accommodated in the cavity of the apparatus and EMF of a desired characteristic applied directly to the plant (or plant part). For example, the apparatus may be configured with a receptacle that can be placed over or around an ear of corn, thereby applying the EMF directly on the plant growing in a field.

As a non-limiting example, the apparatus is used to generate an EMF by AC electric field amplitudes from 1 V/cm to 300 kV/cm and frequencies from a repetition rate from 0.1 Hz to 100 Hz. The duration of application may be 24 hours or longer, or the application duration may be 4-6 hours.

EXAMPLES

The following examples are offered to illustrate, but not to limit the claimed invention.

Example 1. EMF Applied to Plant Cell Culture

The transgenic tobacco (*Nicotiana tabacum*) BY-2 cell line was obtained from RIKEN BioResource Research Center (epd.brd.riken.jp/en/). This cell line expresses green fluorescent protein ("GFP") fused to tobacco α-tubulin. See F. Kumagai, et al., *Fate of nascent microtubules organized at the M/G1 interface, as visualized by synchronized tobacco BY02 cells stably expressing GFP-tubulin: Time-sequence observations of the reorganization of cortical microtubules in living plant cells*, PLANT & CELL PHYS. 42:723-732 (2001). When viewed with a fluorescence microscope, the microtubules fluoresce and enable visualization of microtubule polymerization, including, e.g., spindle fiber and phragmoplast formation during cell division. The BY-GT16 cells were grown in modified LS media supplemented with 0.2 mg/L of 2,4-D. The cells were maintained in the dark at 27° C. on a rotary shaker at 130 rpm, with sub-culturing at 7-day intervals.

To aid visualization and increase the likelihood of observing a plurality of cells undergoing mitosis after S-phase, the BY-GT16 cells were synchronized. To do so, 20 mL of 7-day old suspension culture was transferred into 14 mL of BY-2 media (recipes below in Example 4). To the new suspension, 14 μL aphidicolin (5 mg/mL) was added, and the suspension was incubated in the dark for 24 hours at 25° C. on a rotary shaker at 130 rpm. After incubation, the aphidicolin was removed by washing ten times with 16 mL of sterile BY-2 medium. At the end of the last wash, the cells were resuspended in 16 mL of fresh BY-2 medium and returned the washed suspension to the incubator. BY-2 cells reach maximum mitotic index after approximately eight hours. Generally, peak numbers of cells with phragmoplasts were observed approximately eleven hours after washing. Thus, the plurality of cells was reasonably synchronized.

Figure 3:
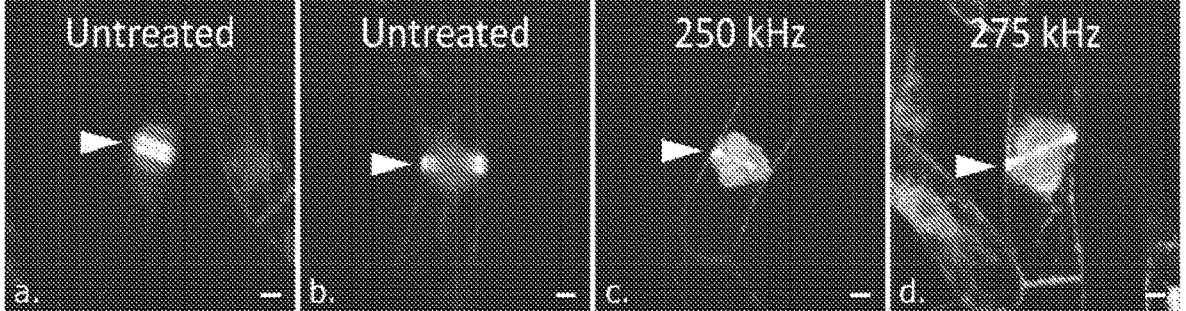
FIG. 3 shows the effect of EMF application on the chromosomes of tobacco BY-2 cells that have been genetically modified to express tubulin monomers fused to a green fluorescent protein ("GFP") domain, according to aspects of this disclosure. (a) (leftmost panel) and (b) (second panel from left) depict cells that have not been subjected to EMF application, including untreated controls and DC field treated controls; (c) (third panel from left) shows cells subjected to a 250 kHz EMF; (d) (rightmost panel) shows cells subjected to a 275 kHz EMF. (a) and (b) show two stages of normal phragmoplast progression during mitosis. (c) and (d) show abnormal phragmoplasts with disorganized microtubules. Arrowheads indicate phragmoplasts; scale bars are equal to 10 μm.

After washing the aphidicolin from the cells, the cells were permitted to restart normal cellular processes for six hours (i.e., the cells were "released"). Next, the population of synchronized cells were prepared for placement in an EMF apparatus (FIG. 1). At that point, 775 μL of cell culture was placed into a 4 mm electroporation cuvette, which was held in place in the cavity of the apparatus using a plastic frame. The plastic frame was designed to fit inside a cavity of the apparatus and was created by 3D-printing. The frame was designed to be placed inside the cavity such that the electrodes (210 and 220) from the Amplifier (200) are able to stably contact the rigid surfaces of the metal plates (Terminals 310 and 320) defining the Cavity (300), which in this instance was configured to hold the cuvette (FIG. 1). The Function Generator (100) was connected to the amplifier and was used to control the frequency (kHz) and field intensity (effective V/cm in the cuvette) of the applied EMF. An optional Oscilloscope (400) was also attached to the For the time period between Hours 7 and 11 after mitotic release of the cells, the EMF was applied to the cells in the cuvette (for a total duration of four hours). After application, the Function Generator (100) was turned off and the cells were removed for viability staining and phragmoplast observation. The remaining cells were fixed in paraformaldehyde for later observation. See FIG. 3.

To determine at what frequency or range of frequencies the BY-2 mitotic structures would be susceptible to the effects of the EMF, frequency tests were conducted in pairs with controls. The controls included a "No Treatment" control where no EMF was applied over the course of several sessions (see "Date of Experiment" column). Since EMF is generated via application of an AC voltage, in some tests, the controls included the application of a corresponding DC voltage. At the conclusion of each treatment, cell viability and phragmoplast count were assessed simultaneously by trypan blue staining and confocal microscopy, respectively. In each case the final data was then normalized to the no treatment control, where the control was held to be 100% viable, and to have the maximum number of phragmoplasts possible. To provide further context, colchicine treatments were done after the EMF experiments, but in the same manner, with similar results obtained to the treatments conducted with EMF application. The EMF application reduced the phragmoplast number at frequencies of 250 and 275 kHz with minimal impact on cell viability.

TABLE 1

| | | | | | | |
|---|---|---|---|---|---|---|
| | | | Frequency testing. | | | |
| Frequency (kHz) | Phragmo-plasts (Per 30 uL Coverslip) | Phragmo-plasts (Normalized to Control) | Live Cells (Per 3 vertical columns) | Dead Cells (Per 3 vertical columns) | Viability (% Live) | Viability (Normalized to Control) |
| 225 | 50 | 41.7 | 508 | 48 | 91.4% | 95.9% |
| 250 | 12 | 2.4 | 728 | 78 | 90.3% | 94.9% |
| 250 | 25 | 4.2 | 782 | 136 | 85% | 87.7% |
| 250 | 12 | 2.6 | 625 | 114 | 85% | 93.0% |
| 275 | 9 | 1.2 | 765 | 156 | 83.1% | 89.1% |
| 275 | 22 | 3.3 | 986 | 223 | 82% | 84.0% |
| 275 | 14 | 3.5 | 634 | 183 | 78% | 85.3% |
| 300 | 49 | 35.3 | 958 | 48 | 95.2% | 102.2% |
| No Treatment | 68 | 68.0 | 862 | 63 | 93.2% | 100.0% |
| No Treatment | 60 | 60.0 | 678 | 34 | 95.2% | 100.0% |
| No Treatment | 148 | 148.0 | 806 | 24 | 97% | 100.0% |
| No Treatment | 56 | 56.0 | 681 | 67 | 91% | 100.0% |
| 1.25 mM Colchicine | 1 | 0.1 | | | | |
| 1.25 mM Colchicine | 7 | 0.9 | | | | |
| 1.25 mM Colchicine | 5 | 0.7 | | | | |
| No Treatment | 19 | 19.0 | | | | |
| No Treatment | 53 | 53.0 | | | | |
| No Treatment | 34 | 34.0 | | | | |
| 1.25 mM Colchicine | | | 732 | 87 | 89.4% | 112.4% |
| 1.25 mM Colchicine | | | 740 | 112 | 86.9% | 94.1% |
| 1.25 mM Colchicine | | | 766 | 120 | 86.5% | 95.4% |
| No Treatment | | | 462 | 119 | 79.5% | 100.0% |
| No Treatment | | | 625 | 52 | 92.3% | 100.0% |
| No Treatment | | | 677 | 70 | 90.6% | 100.0% | positive electrode (210) at the point of contact with the metal plate (310) of the Cavity (FIG. 2). The oscilloscope monitored the sinusoidal variation of the EMF applied to the cells in the cuvette as a function of time.

From the raw data generated during frequency tests, as presented in Table 1, frequency values and ranges were identified where a significant effect of the EMF treatment was observed. Then, additional trials were performed at the identified frequencies. The additional trials included experiments performed in multiple sets at given frequency settings, and the results were then averaged (Table 2). Analysis of the results demonstrated a significant decrease in phragmoplasts in EMF treatments at 250 and 275 kHz similar compared to an untreated "No EMF" control. The results of the EMF treatments were also found to be similar to the results obtained with colchicine treatments. EMF treatments also significantly decreased loss of cell viability while colchicine treatment did not. In other words, colchicine treated cells had a higher loss of viability as compared to EMF treated cells. Each group was compared to the no EMF treatment controls using the Student's T-Test and comparisons where the treatment had a significant decrease in phragmoplast number or in viability are indicated with an asterisk (Table 2; * indicates $p \leq 0.05$).

TABLE 2

| | | | Phragmo- | Average | |
| | | Average | plasts | Viability | Viability |
| | | Phragmoplasts | Standard | (Normal- | Standard |
| n | Treatment | (Normalized) | Deviation | ized) | Deviation |
|---|---|---|---|---|---|
| | | Frequency replicates. | | | |
| 3 | 250 kHz EMF | 3.1* | 1.0 | 87%* | 3% |
| 3 | 275 kHz EMF | 2.7* | 1.3 | 81%* | 3% |
| 3 | 1.25 mM colchicine | 1.0* | 0.5 | 101% | 10% |
| 7 | No EMF | 62.6 | 41.2 | 100% | 0% |

To determine the minimum field intensity required to observe the mitotic inhibition effects of EMF application, the V/cm of the EMF field was varied in further trials using the same experimental setup as described earlier but holding the field frequency constant at 275 kHz. No replicates were performed for these experiments. The reduction in the number of phragmoplasts observed with field intensity 25 V/cm was maintained when the field intensity was lowered to 22.5 V/cm, but not at lower intensities of 12.5 V/cm and 2.5 V/cm. However, the more effective, higher intensity fields also had a larger decrease in the cell viability (Table 3).

TABLE 3

| | | | Live | Dead | | |
| Intensity | Phragmoplasts | Phragmoplasts | Cells (Per | Cells (Per | | Viability |
| (V/cm) all | (Per 30 uL | (Normalized | 3 vertical | 3 vertical | Viability | (Normalized |
| at 275 kHz | Coverslip) | to Control) | columns) | columns) | (% Live) | to Control) |
|---|---|---|---|---|---|---|
| | | Intensity testing. | | | | |
| 2.5 | 66 | 53 | 456 | 44 | 91% | 100% |
| 12.5 | 69 | 58 | 634 | 49 | 93% | 102% |
| 22.5 | 6 | 1 | 561 | 89 | 86% | 91% |
| 25 | 22 | 3 | 986 | 223 | 82% | 84% |
| Maximum | 6 | 1 | 302 | 99 | 75% | 79% |
| No EMF | 82 | 82 | 790 | 79 | 91% | 100% |
| No EMF | 36 | 36 | 692 | 35 | 95% | 100% |
| No EMF | 148 | 148 | 806 | 24 | 97% | 100% |

A range of EMF parameters can be evaluated for different types of plant cells, plant tissues, or whole plants, as the effective frequency and intensity of EMF to disrupt microtubule assembly and interfere with mitosis may vary between cell types, tissue types, and even plant species. The frequencies and intensities used here are by way of illustration for tobacco cells and are not limitations for use in any particular species of plant cell or tissue. For example, a haploid maize embryo may double its chromosomes in the presence of an EMF having a different frequency and intensity than what is illustrated here for tobacco cell culture. Further, duration of application of a given EMF may also affect the chromosome doubling. While appropriate testing may help to optimize results, the principles nevertheless apply.

Example 2. Applying EMF to BMS Cell Culture

A BMS cell culture was obtained and maintained in liquid MS media supplemented with 2 mg/L of 2,4-D as described in Green and Phillips (1975). Five to seven days after subculture, the liquid cell culture was placed in a 0.4 mm gap electroporation cuvette and exposed to EMF application at a frequency of 275 kHz, intensity of 25 V/cm, for a duration of 18 hours with constant shaking at room temperature to disrupt spindle fiber formation and interfere with mitosis. For each treatment, three other tests were also setup from the same culture: (i) 1.25 mM colchicine-treatment, (ii) no treatment culture in an electroporation cuvette, and (iii) no treatment culture that remained in the incubator flask. This duration allows for DNA replication without cell division, thereby causing chromosome doubling.

To measure doubling immediately after treatment, cell culture was prepared for nuclear ploidy analysis first by protoplasting cells for 3 hours in plant protoplast digest/wash buffer (Sigma-Aldrich® D9692) containing 1% cellulase R-10 (GoldBio™ C8001.0001) and 0.1% macerozyme R-10 (GoldBio™ M8002.0001) at 25 C with shaking at 120 rpm. After protoplasting, cells were pelleted by centrifugation at 14000 rpm for 1 min in a tabletop microcentrifuge and protoplast buffer was removed with a pipette. The cells were then resuspended by pipetting in 400 µl of nuclei extraction buffer (Sysmex®, CyStain® UV Precise P Nuclei Extraction Buffer, 05-5002) and mixed with 800 µl of nuclei staining solution (Sysmex®, CyStain® UV Precise P Staining Buffer, 05-5002). The stained nuclei were then passed through a 30 µm filter (Sysmex®, Non-sterile CellTrics® Filter, Green, 04-0042-2316) into the collection cuvette, and the filter rinsed with an additional 800 µl of nuclei staining solution. The cuvette was then loaded into a Sysmex®

Ploidy Analyzer (CyFlow® Ploidy Analyzer, equipped with UV LED 365 nm laser) and data obtained for the entirety of the sample. Untreated BMS cell culture typically has 2-3 ploidy peaks, consistent with the majority of cells existing in a stable ploidy state (peak 1), and a minority of cells being in the process of mitosis and containing double the standard ploidy state (peak 2). After field treatment, cultures consistently displayed 3-4 ploidy peaks indicating the presence of cells with higher levels of genome doubling (peaks 3 and 4). The increase in the proportion of cells represented in the higher level peaks (3 and 4) was associated with a decrease in cells in the lower level peaks (1 and 2), providing direct evidence that field treatment doubled the genomes of cells moving them from peaks 1 and 2 into the category of peaks 3 and 4 (Table 4). To determine whether this change in the relative proportions of cell culture ploidy levels was statistically significant, eight experimental replicates were averaged and the values compared with pairwise T-tests (Table 5 and Table 6). These analyses clearly show that both colchicine and field treatment produce cell cultures with significantly more cells of higher genome content compared to either of the untreated controls (flask or cuvette), providing clear evidence that, like colchicine, field treatment induces genome doubling in plant cells.

TABLE 4

Ploidy analysis results of field treatments on BMS cell suspension cultures.

| Treatment | Proportion of Cells in Each Ploidy Peak (%) | | | |
|---|---|---|---|---|
| | Peak 1 | Peak 2 | Peak 3 | Peak 4 |
| 275 kHz Field | 36.97% | 58.65% | 4.32% | 0.06% |
| 275 kHz Field | 17.66% | 60.96% | 20.14% | 1.24% |
| 275 kHz Field | 20.70% | 61.69% | 16.53% | 1.08% |
| 275 kHz Field | 33.29% | 53.21% | 11.88% | 1.62% |
| 275 kHz Field | 12.99% | 61.95% | 24.49% | 0.57% |
| 275 kHz Field | 21.47% | 57.69% | 19.47% | 1.37% |
| 275 kHz Field | 20.32% | 62.98% | 14.68% | 2.02% |
| 275 kHz Field | 25.24% | 64.97% | 9.46% | 0.33% |
| Colchicine | 38.88% | 57.77% | 3.35% | 0.00% |
| Colchicine | 11.65% | 59.12% | 26.77% | 2.46% |
| Colchicine | 11.29% | 74.64% | 13.43% | 0.64% |
| Colchicine | 27.74% | 57.21% | 13.56% | 1.49% |
| Colchicine | 26.54% | 57.50% | 15.34% | 0.62% |
| Colchicine | 19.87% | 58.10% | 20.30% | 1.72% |
| Colchicine | 35.15% | 54.88% | 8.73% | 1.23% |
| Colchicine | 33.87% | 53.99% | 11.35% | 0.79% |
| Untreated Cuvette | 53.80% | 44.22% | 1.98% | 0.00% |
| Untreated Cuvette | 30.81% | 51.51% | 16.86% | 0.82% |
| Untreated Cuvette | 33.59% | 54.30% | 11.59% | 0.53% |
| Untreated Cuvette | 34.48% | 52.37% | 11.65% | 1.49% |
| Untreated Cuvette | 27.26% | 56.68% | 14.53% | 1.54% |
| Untreated Cuvette | 28.07% | 52.88% | 17.95% | 1.10% |
| Untreated Cuvette | 41.06% | 49.50% | 8.26% | 1.18% |
| Untreated Cuvette | 34.01% | 54.59% | 11.31% | 0.08% |
| Untreated Flask | 60.55% | 37.60% | 1.85% | 0.00% |
| Untreated Flask | 37.92% | 47.60% | 13.34% | 1.14% |
| Untreated Flask | 37.14% | 53.08% | 9.63% | 0.16% |
| Untreated Flask | 48.81% | 45.40% | 5.47% | 0.32% |
| Untreated Flask | 34.41% | 51.12% | 13.39% | 1.08% |
| Untreated Flask | 28.83% | 51.84% | 17.80% | 1.53% |
| Untreated Flask | 41.29% | 47.97% | 9.44% | 1.30% |
| Untreated Flask | 38.06% | 51.53% | 10.06% | 0.35% |

TABLE 5

Average of 8 replicates of field treatment and controls.

| Treatment | Avg Peak1% | Avg Peak2% | Avg Peak3% | Avg Peak4% |
|---|---|---|---|---|
| 275 kHz Field | 23.58% | 60.26% | 15.12% | 1.04% |
| Colchicine | 25.62% | 59.15% | 14.10% | 1.12% |
| Untreated Cuvette | 35.39% | 52.01% | 11.77% | 0.84% |
| Untreated Flask | 40.88% | 48.27% | 10.12% | 0.73% |

TABLE 6

Pairwise T-Tests between averages of 8 replicates (statistically significant values using a p-value ≤ 0.05 cutoff are indicated by *).

| | 275 kHz Field | Colchicine | Untreated Cuvette |
|---|---|---|---|
| Peak 1 T-Tests | | | |
| Colchicine | 0.5539 | | |
| Untreated Cuvette | 0.001* | 0.0121* | |
| Untreated Flask | 0.000* | 0.0024* | 0.0105* |
| Peak 2 T-Tests | | | |
| Colchicine | 0.6833 | | |
| Untreated Cuvette | 0.0014* | 0.0213* | |
| Untreated Flask | 0.0002* | 0.0029* | 0.0033* |
| Peak 3 T-Tests | | | |
| Colchicine | 0.5804 | | |
| Untreated Cuvette | 0.0381* | 0.0213* | |
| Untreated Flask | 0.0064* | 0.0441* | 0.0836 |
| Peak 4 T-Tests | | | |
| Colchicine | 0.7028 | | |
| Untreated Cuvette | 0.3378 | 0.3213 | |
| Untreated Flask | 0.2057 | 0.1154 | 0.5857 |

Example 3. Applying EMF to Maize Callus

Maize callus tissue is obtained, e.g., by the process outlined in Y. I. Dolgykh (1994) *Establishment of Callus Cultures and Regeneration of Maize Plant*, In: Bajaj Y. P. S. (eds) Maize, Biotechnology in Agriculture and Forestry, vol 25, Springer, Berlin, Heidelberg, doi.org/10.1007/978-3-642-57968-4_2, incorporated herein in its entirety. The callus tissue is placed in a suitable receptacle (sometimes referred to as a positioning means), e.g., a cuvette or a Petri dish, and exposed to EMF application at a frequency, intensity, and duration sufficient to disrupt spindle fiber formation and interfere with mitosis. The frequency applied is between 1 kHz and 300 GHz, or between 10 kHz and 1 GHz, or between 100 kHz and 500 kHz. The intensity of EMF application is between 0.5 V/cm and 100 V/cm, or between 1.0 V/cm and 50 V/cm, or between 2.5 V/cm and 25 V/cm. The duration is a time period that is sufficient to prevent mitosis in a sufficient number of cells in the embryo. The duration of EMF application may be at least 24 hours, or at least 12 hours, or at least 8, or at least 6 hours, or at least 4 hours, or at least 2 hours, or at least 1 hour, or at least 30 minutes. This duration allows for DNA replication without cell division, thereby causing chromosome doubling.

Example 4. EMF Applied to Plant Tissues Including Embryos and Microspores

A. Haploid Maize Embryos

Haploid maize embryos are obtained a few days after pollination ("DAP"). Collection may occur 2, 3, 4, 5, 6, 7, 8, 9, 10, 11, 12, 13, 14, 15, 16, 17, 18, 19, 20, 21, 22, 23, 24 or 25 DAP, but preferably occurs between 4 and 20 DAP. Collection may occur manually or with the assistance of a device. See, e.g., U.S. Pat. No. 8,980,632 (incorporated herein by reference in its entirety) and U.S. Pat. No. 9,648, 814 (incorporated herein by reference in its entirety).

The collected maize embryo is placed in plant tissue culture media, such as Murashige and Skoog ("MS" medium), or Chu et al ("N6" medium), or Gamborg et al. ("B5") or other tissue culture salt mixtures or hydroponics (Hoegland) solution, inclusive of carbohydrate sources (e.g., sucrose, maltose, etc.). These facilitate rapid germination, growth and development of the resulting seedlings. Additionally it may be possible to include one or more cytokinin (e.g., Kinetin, Zeatin, 6-Benzylaminopurine, thidiazuron) or auxin (e.g., 2,4-Dichlorphenoxyactic acid, Alpha-Naphtha-lene Acetic Acid, Indole-3-Butyric Acid, or Indole-3-Acetic Acid) or Giberellic Acids (e.g., GA3) plant hormones or various combinations of plant hormones in the plant culture medium for given periods of time to impact cell division within the shoot apical meristem or to enhance growth and development of the resulting seedling.

Haploid embryos may be identified by the presence or absence of pigmentation caused by a color marker, e.g., R1-Navajo anthocyanin marker and other similar markers (R1-scm122, R1-scm2, R1-scm: 3, R1-scm, R1-mb (marbled aleurone), R1-r: standard, R1-Randolph, R1-ch: Stadler, R1-d: Catspaw, A, C, R1-d: Arapaho, R1-nj, (R1-nj: Cudu), (R1-nj: Chase), R1-sc: 124, R1-sup-R1-suppressible, R1 K10-11; R1 M-X1, R1-ch, R1-g, R1-Isk, R1-r, R1-sc122, R1-sc*5691, R1-sk: nc-2, R1-sk, R1-st, etc. and others known in the art.). See, e.g., V. Chaikam et al., *Analysis of effectiveness of R1-nj anthocyanin marker for in vivo haploid identification in maize and molecular markers for predicting the inhibition of R1-nj expression*, THEOR. APPL. GENET. 128 (1): 159-71 (2015). Alternatively, other antho-cyanin markers provide for haploid identification at the seedling stage based the presence or lack of pigmentation in the roots of 3-5 day old seedlings. See Tyrnov and Zaval-ishina, DAN 276:735-738 (1984). Depending on which of a number of known regulatory genes for anthocyanin expres-sion in the embryo axis and scutellar tissue that are employed, the purple coloration in the embryo will appear at different stages of seed and embryo maturity. Thus, not all seed anthocyanin markers are useful in a haploid embryo rescue identification method because the identifying color is not evident in the early stages of embryo development. R1scm2, Rlscm3, Rlscm4, and R1sc122 anthocyanin seed marker haplotypes provide for scutellar pigmentation within 24 hours post embryo rescue of immature embryos (12 DAP). In addition, introgression of the R1scm2 anthocyanin marker haplotype into a maize haploid inducer allows for identification of haploid embryos at least by 12 DAP, and as early as 8, 9, or 10 DAP. It is possible that some of the above color markers may provide for scutellar pigmentation even earlier.

Post-collection, the haploid maize embryo is exposed to EMF application at a frequency, intensity, and duration sufficient to disrupt spindle fiber formation and interfere with mitosis. The frequency applied is between 1 kHz and 300 GHz, or between 10 kHz and 1 GHz, or between 100 kHz and 500 kHz. The intensity of EMF application is between 0.5 V/cm and 100 V/cm, or between 1.0 V/cm and 50 V/cm, or between 2.5 V/cm and 25 V/cm. The duration is a time period that is sufficient to prevent mitosis in a sufficient number of cells in the embryo. The duration of EMF application may be at least 24 hours, or at least 12 hours, or at least 8, or at least 6 hours, or at least 4 hours, or at least 2 hours, or at least 1 hour, or at least 30 minutes. This duration allows for DNA replication without cell division, thereby causing chromosome doubling.

Embryo Rescue & Germination steps: Immature embryos are carefully isolated from sterilized ears and placed in petri plates containing plant tissue culture media as described previously. After identification of haploid embryos and application of the doubling treatment, embryos are then incubated in a growth chamber (16-h photoperiod, 226 µE/m², 26° C.) until stage V3. All the plantlets are then transferred to pots containing a soil or soilless mixture and grown in a growth chamber or greenhouse (16-h photope-riod, 226 µE/m², 26° C. and 90% humidity) for hardening for 1 week. After that, plantlets were transferred to 5 gallon pots and grown in a greenhouse (16-h photoperiod, 650 µE/m², 30-20° C. day/night temperature) to maturity.

B. Plant Microspores

Flowers with anthers at the mid to late uninucleate microspore stage are harvested and subjected to an optional mannitol, salt, cold, or heat stress treatment, then sterilized in a solution of ethanol and sodium hypochlorite. Microspores are released from the anthers using mechanical perturbation (for instance, in a blender), then recovered through a series of filtration and centrifugation steps. See U.S. Pat. No. 5,322,789 (filed Dec. 21, 1992), incorporated herein by reference. The resulting isolate is resuspended in a maltose or other sugar-based gradient and subjected to an additional centrifugation to separate pure microspores. Those isolated microspores are then washed, quantified, and plated into specialized culture media, e.g., as outlined in Zheng M. Y., Weng Y., Sahibzada R., Konzak C. F. (2003) *Isolated microspore culture in maize (Zea mays L.), produc-tion of doubled-haploids via induced androgenesis*, In: DOUBLED HAPLOID PRODUCTION IN CROP PLANTS Maluszynski M., Kasha K. J., Forster B. P., Szarejko I. (eds). Springer, Dordrecht; doi.org/10.1007/978-94-017-1293-4_15, incor-porated herein by reference, before incubation in the dark. A proportion of these cultured microspores that successfully convert to embryo-like structures (ELS) are moved to the next media step for green plant regeneration. ELS resulting in green plants are then treated with EMF fields to produce doubled haploid plants that are then grown into mature plants that are self-pollinated to produce seeds. Alterna-tively, the ELS stage plantlets are treated with the EMF to induce genome doubling. Alternatively, the isolated microspores are treated with the EMF to induce genome doubling at the early stage, soon after microspore isolation from the anther. Alternatively, instead of isolated microspores, whole anthers are isolated and cultured in a similar process as the microspores, and an EMF treatment is used to induce genome doubling during the culture process.

Example 5. EMF Application to Seedlings, Young Plants, or Mature Plants

Electrodes from the Amplifier stably contact the metal plates of a Cavity, in this instance, a small space in which a plant stem containing a shoot apical meristem can be placed. The Function Generator is connected to the amplifier and is used to control the frequency (kHz) and field intensity (effective V/cm in the space) of the applied EMF. An optional Oscilloscope is also attached to the positive elec-trode at the point of contact with the metal plate of the Cavity. The oscilloscope monitored the EMF voltage applied to the cells in the cuvette. A portion of the plant that contains the vegetative, axillary, or reproductive (inflores-cence) or floral meristems is placed into the space between the electrodes (in the Cavity between the metal plates) and the EMF is applied. The plant is then cultured or grown to the flowering stage and the resulting flowers are used for self-pollination or outcrossing. In this example, the plant may be a haploid plant or a plant with higher ploidy. It may be an interspecific hybrid between two different species, or an intraspecific hybrid, or a chromosome addition line, or any other plant.

Example 6. Construction of the EMF Apparatus

Details on insulated electrodes. In some examples, the EMF may be applied by conductive coupling, with the electrodes in the cuvette in direct contact with the cell suspension; however, this need not be the case. EMFs may also be applied using capacitive coupling, where one or both electrodes do not directly contact the suspension. Avoiding direct electrode contact with the suspension reduces the risk of sample contamination from the release of ions from the electrodes into the sample. This could also aid in ensuring sterility of the treated sample since the sample could be closed to atmosphere. Using capacitive coupling reduces the electric field that reaches the biological cell, which may reduce the intensity of the biological effect and necessitate increasing the applied voltage compared to what is applied above to the cuvette. Capacitive coupling may be achieved by placing the electrodes on either or both sides of a Petri dish and applying the EMF across this to induce the desired effect. Achieving similar electric field delivery to the sample as in the conductive coupling may necessitate applying stronger electric fields and even applying them as pulses with duration from 10 ns to 1 ms, applied electric field from 1 V/cm to 300 kV/cm, rise- and fall-times from 0.5 ns to 5000 ns, and repetition rate from 0.1 Hz to 100 Hz across the Petri dish. Prior calculations demonstrated that capacitive coupling may reduce the transmembrane potential induced by the applied field by as much as 3-5 orders of magnitude. In those cases, the transmembrane potential became bipolar, meaning that biological cells exposed to electric pulses under capacitive coupling will receive similar electric field exposure to the EMF described above but with requiring a much higher applied voltage.

Details on needle electrode placement. In vivo cancer treatment with electric pulses often prohibits the use of standard parallel plate geometries, which makes it challenging to achieve uniform electric fields to the treated tissues. To achieve a more uniform field distribution, arrays of "needle" shaped electrodes can be used instead. An array of needle electrodes may be placed around the callus or sample in a Petri dish with the needles' geometries, orientation, and placement adjusted to achieve a uniform distribution of electric field.

It is understood that the examples and embodiments described in the present disclosure are for illustrative purposes only and that various modifications or changes in light thereof will be suggested to persons skilled in the art and are to be included within the spirit and purview of this application and scope of the appended claims. All publications, patents, and patent applications cited in the present disclosure are hereby incorporated by reference in their entirety for all purposes.

What is claimed is:

1. A method for chromosome doubling in a plant cell, the method comprising:
   a) applying an electromagnetic field ("EMF") to a plant cell in vitro; and
   b) allowing the EMF to disrupt mitosis;
   wherein the plant cell replicates its chromosomes without undergoing cell division, thereby obtaining a plant cell having doubled chromosomes,
   wherein the EMF frequency is applied at a range of 100 kHz to 500 kHz, inclusive,
   wherein the EMF intensity is applied at a range of 0.5 V/cm to 100 V/cm, and
   wherein the EMF is applied at a duration selected from a group consisting of (i) at least a duration equivalent to prophase of mitosis for the plant cell; (ii) a duration equivalent to an entire mitosis cycle for the plant cell; and (iii) about 5 hours.

2. The method of claim 1, wherein the EMF disrupts mitosis by disrupting spindle fiber formation.

3. The method of claim 1, wherein the EMF has a waveform, and wherein parameters of the EMF include one or more of frequency, periodicity, and amplitude of the waveform.

4. The method of claim 1, wherein the duration equivalent to the prophase of mitosis is approximately 25 minutes for a maize cell.

5. The method of claim 1, wherein the plant cell is a monocot or a dicot.

6. The method of claim 5, wherein the monocot is selected from the group consisting of maize, wheat, rice, sorghum, onion, and barley.

7. The method of claim 5, wherein the dicot is selected from the group consisting of soybean, sunflower, tomato, tobacco, cucurbits, brassicas, lettuce, petunia, rose, and calliope.

8. The method of claim 1, wherein the plant cell is a haploid plant cell.

9. The method of claim 1, wherein the plant cell is a meristematic cell.

10. The method of claim 1, wherein the plant cell is a gamete cell.

11. The method of claim 1, wherein the plant cell is comprised within a tissue sample.

12. The method of claim 11, wherein the tissue sample is a plant embryo.

13. The method of claim 11, wherein the tissue sample is selected from the group consisting of a flower, an ear, a tassel, a seed pod, a seed, an embryo, and a portion of any of the preceding provided the tissue sample comprises viable cells.

14. A method for producing a doubled-haploid plant cell, comprising:
   a) obtaining a haploid plant cell;
   b) subjecting the haploid plant cell to an electromagnetic field ("EMF") in vitro; and
   c) allowing the EMF to disrupt mitosis in the haploid plant cell;
   whereby the haploid plant cell replicates its chromosomes yet fails to undergo cell division, thereby producing the doubled-haploid plant cell,
   wherein the EMF is an AC field with an applied electric field from 0.5 V/cm to 100 V/cm with a frequency from 100 kHz to 500 kHz, or
   wherein the EMF is an electric pulse with duration from 10 ns to 1 ms, an applied electric field from 1 V/cm to 300 kV/cm, rise- and fall-times from 0.5 ns to 5000 ns, and a repetition rate from 0.1 Hz to 100 Hz.

15. The method of claim 14, wherein the plant cell is a monocot or a dicot.

16. The method of claim 15, wherein the monocot is selected from the group consisting of maize, wheat, rice, sorghum, onion, and barley.

17. The method of claim 15, wherein the dicot is selected from the group consisting of soybean, sunflower, tomato, tobacco, cucurbits, brassicas, lettuce, *petunia*, rose, and calliope.

18. The method of claim 14, wherein the plant cell is a meristematic cell.

19. The method of claim 14, wherein the plant cell is a gamete cell.

20. The method of claim 14, wherein the plant cell is comprised within a tissue sample.

21. The method of claim 20, wherein the tissue sample is a plant embryo.

22. The method of claim 20, wherein the tissue sample is selected from the group consisting of a flower, an ear, a tassel, a seed pod, a seed, an embryo, and a portion of any of the preceding provided the tissue sample comprises viable cells.

\*   \*   \*   \*   \*